United States Patent [19]

McMillan, Jr. et al.

[11] Patent Number: 5,106,749

[45] Date of Patent: Apr. 21, 1992

[54] FUNGUS AND PROCESS FOR GROWTH PROMOTION IN PLANTS

[75] Inventors: Robert T. McMillan, Jr.; Komaratchi R. Narayanan, both of Homestead, Fla.

[73] Assignee: University of Florida, Gainesville, Fla.

[21] Appl. No.: 265,633

[22] Filed: Nov. 1, 1988

[51] Int. Cl.⁵ .................. C12N 1/14; A01N 63/04; A01H 15/00

[52] U.S. Cl. .................. 435/254; 424/93 Q; 435/911; 47/58; 71/65; 71/79; 71/77

[58] Field of Search .............. 71/3, 65, 77; 47/58; 435/911, 255, 254; 424/93

[56] References Cited

U.S. PATENT DOCUMENTS 4,550,527 11/1985 Hall et al. .................. 47/58

OTHER PUBLICATIONS

Garrett, S. D. (1970) Pathogenic Root-Infecting Fungi, University Press, 1970, pp. 45–46.
Nemec, et al. (1982) J. Amer. Soc. Hort. Sci. 107:177–180.
Chang, et al. (1986) Plant Disease 70:145–148.
Khachatourians (1986) Tibtech, May 1986: pp. 120–124.
Custom Applicator (May 1986) vol. 16, pp. 40–42.

Primary Examiner—Jacqueline Stone
Assistant Examiner—Che S. Chereskin
Attorney, Agent, or Firm—Saliwanchik & Saliwanchik

[57] ABSTRACT

This invention pertains to the identification and isolation of a novel fungus which can be used for growth stimulation in plants. A method of promoting plant growth using the novel fungus is provided.

6 Claims, 3 Drawing Sheets

FUNGUS AND PROCESS FOR GROWTH PROMOTION IN PLANTS

BACKGROUND OF THE INVENTION

Root-infecting, nonpathogenic fungi capable of promoting plant growth have been demonstrated, the classic examples being various mycorrhizae (Garrett, S. D. [1970] Pathogenic Root-Infecting Fungi, University Press, p. 294; Harley, J. L., and S. E. Smith [1983] Mycorrhizal Symbiosis, Academic Press, London). Mycorrhizae are known to increase photosynthetic and water use efficiency and nutrient uptake under nutrient-deficient soils (Graham, J. H. et al. [1987] New Phytol. 105:411–419; Nemec, S. and G. Guy [1982] J. Am. Soc. Hort. Sci. 107:177–180). They are also known to produce auxins (Slankis, V. [1958]; Moser [1959]) and cytokinins (Miller, C. O. [1971] In Mycorrhizae, E. Hacskaylo, ed.).

Pathogenic fungi causing growth promotion in plants are also known. In fact, gibberellin, one of the major growth promoting hormones in plants, was first isolated from Gibberella fujikuroi, a fungus which infects rice plants (Cross, B. E. [1954] J. Chem Soc. 4670–4676). Rademacher and Graebe (Rademacher, W., and J. E. Graebe [1979] Biochem. Biophys. Res. Commun. 91:35–40) reported the production of gibberellin $A_4$ by Sphaeclona manihoticola which is a fungal pathogen of cassava.

BRIEF SUMMARY OF THE INVENTION

The subject invention concerns a novel fungus which can be used for growth stimulation in plants. More specifically, the subject invention concerns a novel isolate tentatively identified as *Sphaeropsis tumefaciens*, and hereinafter referred to as Bud-1.

The novel fungus of the subject invention can be used to treat plants in order to promote the growth of the treated plant. The method of the subject invention results in increased root mass and vegetative growth.

DETAILED DESCRIPTION OF THE INVENTION

The subject invention relates to increased plant growth obtained by treating plants with a novel fungus. The fungus described here is an isolate of *Sphaeropsis tumefaciens*. This isolate has been designated Bud-1.

The novel fungus of the invention, Bud-1, has been deposited in the American Type Culture Collection (ATCC), 12301 Parklawn Drive, Rockville, Md. 20852.

| Deposit | Accession No. | Deposit date |
|---|---|---|
| *Sphaeropsis tumefaciens* | ATCC 20908 | October 28, 1988 |
| Bud-1 | | |

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The wild type *S. tumefaciens* is known to cause galls in Callistemon and other species (Jarvis, P. G. [1971] In Plant Photosynthetic Activity: Manual of Methods. Z. Sestack, J. Catsky, P. G. Jarvis, eds., Junk, The Hague, pp. 566–631; Ridings, W. H., and R. B. Marlatt [1976] Proc. Fla. State Hort. Soc. 89:302–303). Surprisingly, the novel isolate of *S. tumefaciens* which is described here is not pathogenic.

Figure 1:
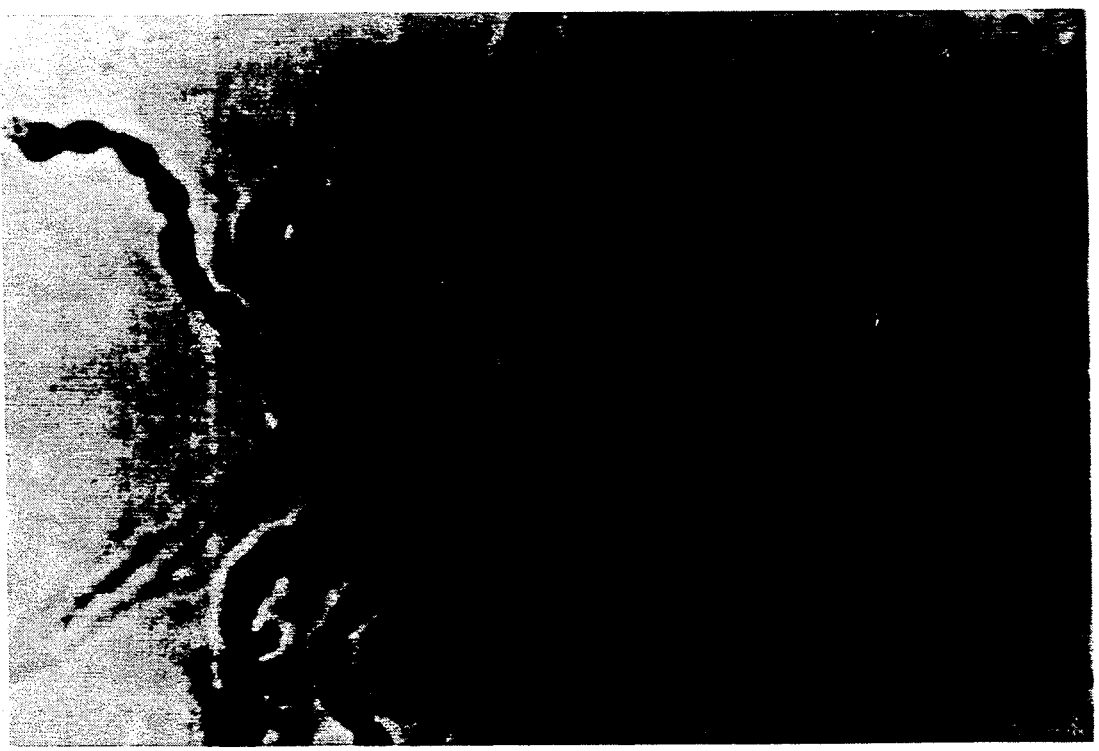
FIG. 1—Non-pathogenic, putative *Sphaeropsis tumefaciens* isolate showing hyphae characteristic of its growth.
Figure 2:
FIG. 2—Uninoculated and root-inoculated *Callistemon viminalis* seedlings showing growth stimulation by the non-pathogenic fungus.
Figure 3:
FIG. 3—Uninoculated and leaf-inoculated *Callistemon viminalis* seedlings showing growth promotion by non-pathogenic *Sphaeropsis tumefaciens*.

Advantageously, Bud-1 was found to be responsible for significant growth promotion in axenic culture when roots or leaves of Callistemon seedlings were infected (FIGS. 1 and 2). When compared to noninoculated controls, the root-infected seedlings were 2–5 times taller with greater root mass and vegetative growth (FIG. 1). The growth promoting effect of Bud-1 was also apparent, although to a lesser degree, in leaf-infected Callistemon seedlings (FIG. 2). Callistemon seedlings infected with pathogenic *S. tumefaciens* either in the roots or leaves did not survive for more than 7–10 days.

The growth promoting effect of Bud-1 was not restricted to bottle brush (Myrtaceae) but was also observed in citrus, Eucalyptus, Melalueca, and Cattleya (orchid).

The fungus of the subject invention can be grown on slants and in liquid broth (25° C. to 32° C.). One acceptable medium of growth on an agar slant is Bacto Oatmeal Agar. This medium can be prepared by dissolving 72.5 g of the agar in 1000 ml cold distilled water. The mixture is then heated to boiling with constant stirring. Finally, the medium is sterilized in an autoclave for 15 minutes at 15 pounds of pressure and 121° C.

Alternatively, 45 g of malt agar can be dissolved in 1000 ml cold distilled water followed by boiling and sterilization as described above.

For liquid broth, 15 g of Malt Extract Broth (DIFCO) can be dissolved in 1000 ml of cold distilled water, followed by boiling and sterilization as described above.

The novel compositions of the invention can be used to promote plant growth by standard means of application, for example, by spraying onto the plants. Generally, the *S. tumefaciens* will be used in the spore form. However, if desired, fragmented mycelium can also be used. Where spores are used, a spore concentration of from about $1 \times 10^3$ to about $1 \times 10^6$ spores/ml can be used. The amounts of fragmented mycelium to be used can be readily determined by routine experimentation.

Though spores are the preferred form of the fungi, the fungi also can be formulated as fragmented mycelia and applied as foliar sprays.

Spores or mycelial fragments of *S. tumefaciens*, ATCC 20908, can be combined with various chemical additives to increase plant growth. Application rates of these chemicals would be expected to be less than or equal to the rates recommended for conventional use.

As an alternative means of applying the compositions of the invention, the tank-mix combinations can contain an emulsifiable crop oil comprising a non-phytotoxic crop oil and an emulsifier. Suitable emulsifiable crop oils are marketed under the tradenames SOY-DEX TM (Helena Chemical Co., Memphis, TN), a vegetable oil surfactant containing vegetable oil and a non-ionic blend of alkoxylated alkylphenols and fatty acids; AGRI-DEX TM (Helena Chemical Co.), a non-ionic spray adjuvant containing paraffin base petroleum oil, polyol fatty esters and polyethoxylated derivatives thereof; and SUN SPRAY TM (Sun Refining & Marketing Co., Marcus Hook, Pa.), a 100% light paraffinic distillate. Example of non-phytotoxic crop oils are canola oil, soybean oil, cottonseed oil, peanut oil, corn oil, coconut oil, castor oil, esters (1–4C) of these oils, and blends of these oils and esters.

The emulsifier (surfactant) which can be used includes anionic, cationic, and non-ionic agents. See "Detergents and Emulsifiers" 1971 Annual by John W. McCutcheon, Inc. for a good disclosure of suitable emulsifiers. Generally, 1-10% by weight of the emulsifiers can be used. Specific adjustments can be made by persons skilled in the art using routine procedures.

The novel isolate of the subject invention can also be used as a fungal vector for plant transformation. This capability is evidenced somewhat by the fact that the wild type *S. tumefaciens* causes galls and Bud-1 is able to cause growth promotion upon application to leaves. Thus, it is believed that the new isolate can serve as a fungal vector for plant transformation with broad specificity.

We claim:

1. A biologically pure culture of the fungus *Sphaeropsis tumefaciens*, referred to as Bud-1, and having all of the identifying characteristics of ATCC 20908.

2. A composition for promoting plant growth, said composition comprising an effective amount of the novel isolate of *Sphaeropsis tumefaciens* referred to as Bud-1, and having all of the identifying characteristics of ATCC 20908.

3. A composition, according to claim 2, where said composition further comprises an agriculturally acceptable carrier.

4. A process for promoting plant growth, said process comprising the application of an effective amount of a novel isolate of *Sphaeropsis tumefaciens*, referred to as Bud-1 and having all of the identifying characteristics of ATCC 20908, onto said plant or onto the situs of said plant.

5. A process, according to claim 4, wherein said *Sphaeropsis tumefaciens* is applied in combination with an agriculturally acceptable carrier.

6. A process, according to claim 4, where said plant is selected from the group consisting of Callistemon, Melaleuca, Eucalyptus, Citrus, and Cattleya (orchid).

* * * * *

UNITED STATES PATENT AND TRADEMARK OFFICE
CERTIFICATE OF CORRECTION

PATENT NO.    :    5,106,749

DATED         :    April 21, 1992

INVENTOR(S)   :    Robert T. McMillan, Jr., Komaratchi R. Narayanan

It is certified that error appears in the above-identified patent and that said Letters Patent is hereby corrected as shown below:

Column 1: line 67 through
Column 2: line 4:

"Deposit                            Accession No.              Deposit date
*Sphaeropsis tumefaciens* ATCC 20908                           Oct. 28, 1988
Deposit                             Accession No.              Deposit date
Bud-1"
        should read
--Deposit                           Accession No.     Deposit date
*Sphaeropsis tumefaciens* Bud-1     ATCC 20908        Oct. 28, 1988--.

Signed and Sealed this

Twenty-ninth Day of June, 1993

Attest:

MICHAEL K. KIRK

Attesting Officer      Acting Commissioner of Patents and Trademarks